(12) United States Patent
Brands et al.

(10) Patent No.: US 6,479,667 B2
(45) Date of Patent: Nov. 12, 2002

(54) CRYSTALLINE FORMS OF ANTIBIOTIC SIDE CHAIN INTERMEDIATES

(75) Inventors: Karel J. M. Brands, Jersey City; Karen M. Conrad, Union; John M. Williams, Belle Mead, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/796,006

(22) Filed: Feb. 28, 2001

(65) Prior Publication Data

US 2002/0062032 A1 May 23, 2002

Related U.S. Application Data

(60) Provisional application No. 60/186,194, filed on Mar. 1, 2000.

(51) Int. Cl.[7] ............................................. C07D 207/08
(52) U.S. Cl. .......................................................... 548/537
(58) Field of Search ........................................... 548/537

(56) References Cited

U.S. PATENT DOCUMENTS

| 5,648,501 A | 7/1997 | Brands |
| 5,965,747 A | 10/1999 | Brands et al. |
| 6,063,931 A | 5/2000 | Brands et al. |

FOREIGN PATENT DOCUMENTS

| WO | WO 97/06154 | 2/1997 |

*Primary Examiner*—Robert Gerstl
(74) *Attorney, Agent, or Firm*—Sylvia A. Ayler; Valerie J. Camara; Mark R. Daniel

(57) ABSTRACT

Crystalline 2S-cis-3-[[(4-mercapto-2-pyrrolidinyl)carbonyl]-amino]benzoic acid and salts and solvates thereof are disclosed. A crystalline type is described.

3 Claims, 1 Drawing Sheet

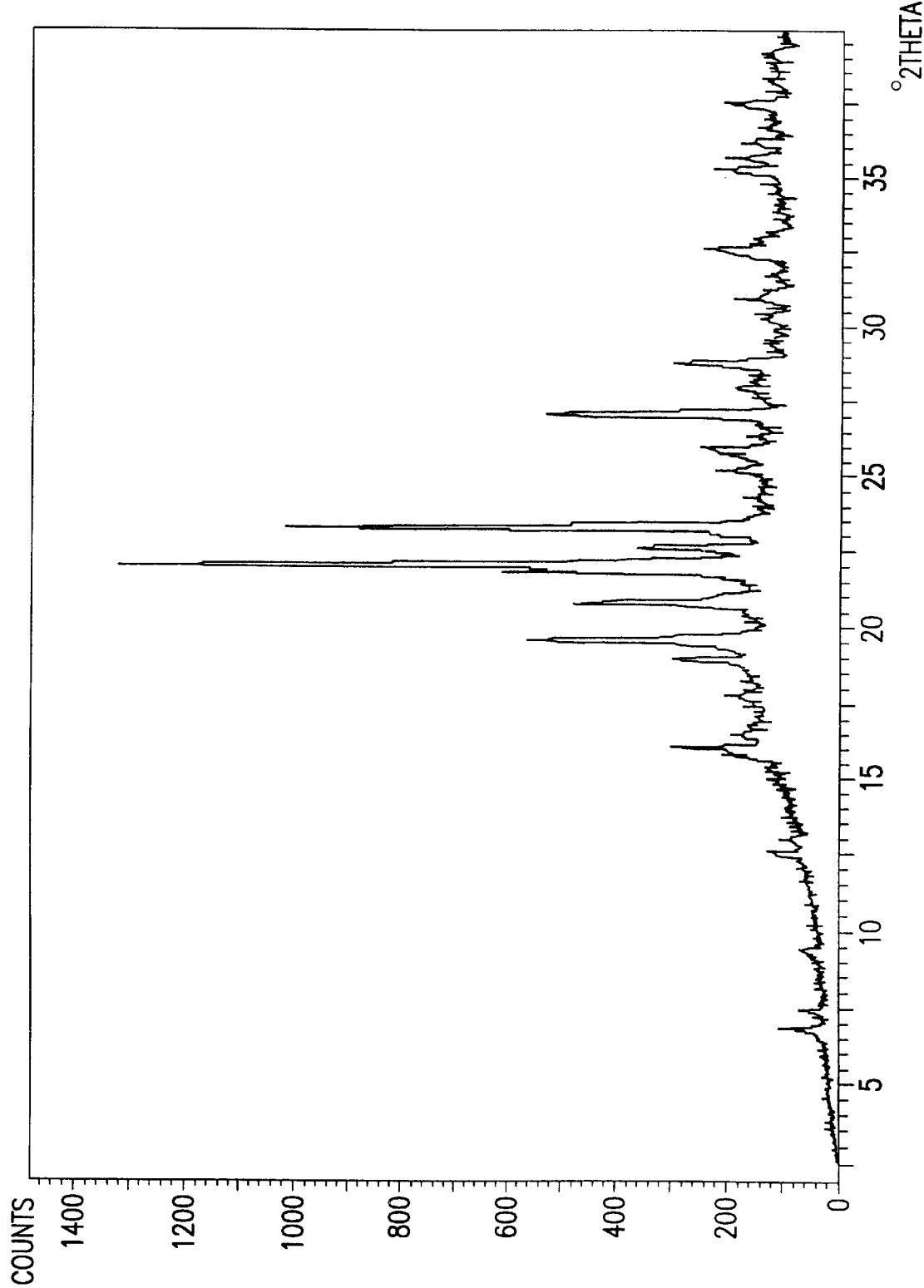

CRYSTALLINE FORMS OF ANTIBIOTIC SIDE CHAIN INTERMEDIATES

This application claims the benefit of U.S. Provisional Application No. 60/186,194, filed Mar. 1, 2000.

BACKGROUND OF THE INVENTION

Crystalline forms of intermediates for carbapenem antibiotics are desirable from a stability and purity standpoint. These compounds facilitate the synthesis of carbapenem antibiotics on a commercial scale.

In the present invention, crystalline forms of the compound 2S-cis-3-[[(4-mercapto-2-pyrrolidinyl)carbonyl]-amino] benzoic acid have been discovered and characterized. Crystalline 2S-cis-3-[[(4-mercapto-2-pyrrolidinyl)carbonyl]-amino]benzoic acid and salts and solvates thereof are disclosed. The compounds can generally be synthesized taking into account the disclosure of U.S. Pat. No. 5,648,501 granted Jul. 15, 1997 and U.S. Pat. No. 5,963,747, granted Oct. 12, 1999 (both incorporated herein by reference).

SUMMARY OF THE INVENTION

Crystalline 2S-cis-3-[[(4-mercapto-2-pyrrolidinyl)carbonyl]-amino]benzoic acid as well as salts and solvates thereof are disclosed.

BRIEF DESCRIPTION OF THE DRAWINGS

The invention is described in connection with the following drawings, of which:

FIG. 1 is an X-Ray Powder Diffraction pattern of Compound I, as the NEP solvate.

DETAILED DESCRIPTION OF THE INVENTION

The compound has the following structural formula:

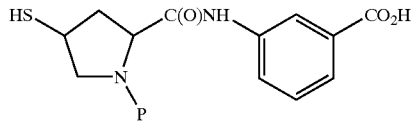

I wherein P represents H or a protecting group.

The salt form of the compound can be protonated as shown in the following:

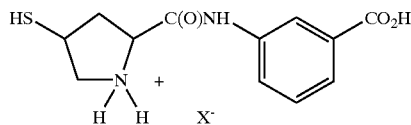

wherein $X^-$ represents a negatively charged counterion. The salt forms can also be present in the form of a solvate.

The crystalline forms of the compound are characterized below by virtue of their X-Ray Powder Diffraction (XRPD) patterns. The XRPD patterns were collected on a Philips PW 3710 MPD control automated powder diffractometer. The x-ray generator employed a copper target, an accelerating potential of 45 kV and a filament emission of 40 mA. Diffraction patterns were collected from about 2° to about 40°.

The NEP (1-ethyl-2-pyrrolidinone) was characterized as having an XRPD pattern at 4.490, 4.242, 4.042, 3.993, 3.912, 3.790 and 3.274 angstroms. More complete XRPD data pertaining to the compound is shown below in Table 1.

TABLE 1

| Peak No. | D Spac (Ang) | I/Imax (%) |
|---|---|---|
| 1 | 29.75602 | 0.21 |
| 2 | 16.75182 | 1.11 |
| 3 | 12.75496 | 5.80 |
| 4 | 11.76271 | 3.05 |
| 5 | 9.31275 | 3.01 |
| 6 | 6.98309 | 4.32 |
| 7 | 6.75560 | 2.25 |
| 8 | 5.48109 | 16.07 |
| 9 | 5.33846 | 7.98 |
| 10 | 4.95477 | 8.18 |
| 11 | 4.63685 | 16.77 |
| 12 | 4.49049 | 36.16 |
| 13 | 4.24207 | 30.18 |
| 14 | 4.04244 | 43.65 |
| 15 | 3.99347 | 100.00 |
| 16 | 3.91155 | 24.03 |
| 17 | 3.78976 | 72.59 |
| 18 | 3.51266 | 9.31 |
| 19 | 3.41712 | 12.17 |
| 20 | 3.27397 | 34.65 |
| 21 | 3.18178 | 7.32 |
| 22 | 3.09132 | 17.61 |
| 23 | 3.01996 | 2.84 |
| 24 | 2.94164 | 3.82 |
| 25 | 2.88451 | 6.75 |
| 26 | 2.80895 | 3.99 |
| 27 | 2.73399 | 13.22 |
| 28 | 2.53685 | 11.72 |
| 29 | 2.51050 | 8.22 |
| 30 | 2.47204 | 5.41 |
| 31 | 2.44191 | 3.40 |
| 32 | 2.39183 | 8.16 |
| 33 | 2.35108 | 3.17 |
| 34 | 2.31168 | 4.33 |
| 35 | 2.29334 | 4.47 |

Notes:
Generator settings: 45 kV, 40 mA
Cu alpha 1, 2 wave lengths 1.54060, 1.54439 Ang The XRPD pattern corresponding to Table I is shown as FIG. 1.

The crystalline compound of the present invention is useful in various salt forms, for the synthesis of carbapenem compounds that are in turn useful for the treatment of bacterial infections in animal and human subjects. Factors which are important in the salt selection, are cost of the raw materials, ease of crystallization, purity, yield, stability, hygroscopicity and flowability of the resulting intermediate.

Typically the intermediate compound is protonated, and is found in association with a negatively charged counterion, represented by the generic $X^-$. There are various possibilities for the charge balancing counterion $X^-$. Representative examples of such counterions are the following: acetate, adipate, aminosalicylate, anhydromethylenecitrate, ascorbate, aspartate, benzoate, benzenesulfonate, bicarbonate, bisulfate, bromide, citrate, camphorate, camphorsulfonate, carbonate, chloride, digluconate, edetate, edisylate, estolate, ethanesulfonate, fumarate, glucoheptanoate, gluconate, glutamate, glycerophosphate, glycolate, hydroxynaphthoate, 2-hydroxyethanesulfonate, iodide, lactate, lactobionate, malate, maleate, mandelate, methylenebis(salicylate), mucate, methanesulfonate, napadisylate, napsylate, pamoate, pantothenate, pectinate, phosphate/diphosphate, polygalacturonate, propionate, salicylate, stearate, succinate, sulfate, tartrate, triflate, tosylate and undecanoate. Other anionic species will be apparent to the ordinarily skilled chemist. The preferred counterion is chloride.

The preferred form of the crystalline compound is the NEP solvate form.

The compound can be produced in accordance with the following non-limiting example.

EXAMPLE ONE

A. Synthesis

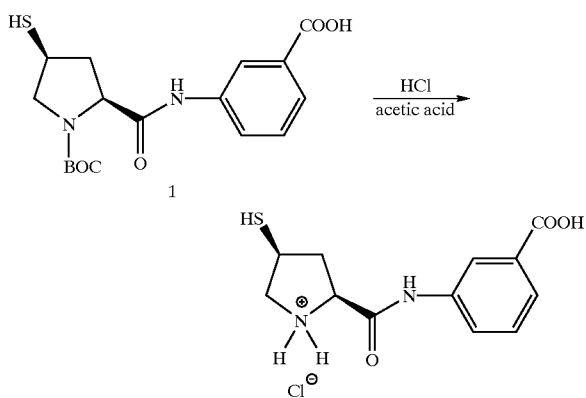

The BOC protected sidechain 1 (prepared according to the teachings of PCT WO97/06154 published on Feb. 20, 1997) was dissolved in 1.5 L of a 1 N solution of dry hydrogen chloride in acetic acid (30 min). Gas evolution was observed and the reaction product slowly crystallized. After filtering, washing (with acetic acid and hexane) and drying 137 g of non-solvated product was obtained.

B. Recrystallization Procedures
NEP Solvate

A slurry of the above product (50 g) in N-ethyl pyrrolidinone (250 mL) was heated to 45° C. to effect complete dissolution. Toluene (250 mL) was added slowly to the resulting solution. After aging at 40° C. for 40 min solids were produced and the mixture was allowed to cool to ambient temperature. After an additional age of 4 h the product was filtered, washed with NEP/toluene 1/1 and toluene, and dried in vacuo to yield the NEP solvate (80% yield).

What is claimed is:

1. Crystalline 2S-cis-3-[[(4-mercapto-2-pyrrolidinyl)carbonyl]amino]benzoic acid as the hydrochloride salt NEP solvate.

2. Crystalline 2S-cis-3-[[(4-mercapto-2-pyrrolidinyl)carbonyl]amino]benzoic acid in accordance with claim 1, having an X-ray powder diffraction pattern in accordance with FIG. 1.

3. Crystalline 2S-cis-3-[[(4-mercapto-2-pyrrolidinyl)carbonyl]amino]benzoic acid in accordance with claim 1, having an X-ray powder diffraction pattern:

| D Spac (Å)-NEP Solvate |
| --- |
| 29.75602 |
| 16.75182 |
| 12.75496 |
| 11.76271 |
| 9.31275 |
| 6.98309 |
| 6.75560 |
| 5.48109 |
| 5.33846 |
| 4.95477 |
| 4.63685 |
| 4.49049 |
| 4.24207 |
| 4.04244 |
| 3.99347 |
| 3.91155 |
| 3.78976 |
| 3.51266 |
| 3.41712 |
| 3.27397 |
| 3.18178 |
| 3.09132 |
| 3.01996 |
| 2.94164 |
| 2.88451 |
| 2.80895 |
| 2.73399 |
| 2.53685 |
| 2.51050 |
| 2.47204 |
| 2.44191 |
| 2.39183 |
| 2.35108 |
| 2.31168 |
| 2.29334. |

* * * * *